United States Patent [19]

Cross et al.

[11] Patent Number: 4,936,838
[45] Date of Patent: Jun. 26, 1990

[54] FEMALE EXTERNAL URINAL DEVICE

[75] Inventors: David E. Cross, Rustington; Elizabeth M. Thurston, Bedford, both of England

[73] Assignee: Smiths Industries Public Limited Company, London, England

[21] Appl. No.: 232,747

[22] Filed: Aug. 16, 1988

[30] Foreign Application Priority Data

Aug. 20, 1987 [GB] United Kingdom ................. 8719683

[51] Int. Cl.⁵ ............................................... A61F 5/44
[52] U.S. Cl. ..................................... 604/329; 128/761
[58] Field of Search ............................... 604/329–331, 604/347, 355, 385.1; 128/761; 4/144.1–144.4

[56] References Cited

U.S. PATENT DOCUMENTS

| | | | |
|---|---|---|---|
| 2,331,355 | 10/1943 | Strongson | 604/385.1 |
| 3,512,185 | 5/1970 | Ellis | 4/110 |
| 4,194,508 | 3/1980 | Anderson | 604/329 |
| 4,610,675 | 9/1986 | Triunfol | 604/329 |
| 4,758,240 | 7/1988 | Glassman | 604/379 |
| 4,781,713 | 11/1988 | Welch et al. | 604/385.1 |

FOREIGN PATENT DOCUMENTS

| | | |
|---|---|---|
| 0109217 | 5/1984 | European Pat. Off. . |
| 1253497 | 11/1971 | United Kingdom . |
| 2129304 | 5/1984 | United Kingdom . |
| 2129305 | 5/1984 | United Kingdom . |
| 2129686 | 5/1984 | United Kingdom . |
| 2184023 | 6/1987 | United Kingdom . |

Primary Examiner—J. L. Kruter
Attorney, Agent, or Firm—Pollock, VandeSande and Priddy

[57] ABSTRACT

A female external urine collection device has a moulded plastics tray that supports an insert or a planar top with an upper surface that contacts the wearer. The upper surface is shaped with an annular wall that engages around the vulva and an opening with a urine-resistant surface within the wall. The opening communicates with an outlet orifice in the tray so that discharge of urine is contained within the wall and flows to the outlet. A longitudinal ridge extends posteriorly of the wall and is located between the buttocks of the user.

7 Claims, 3 Drawing Sheets

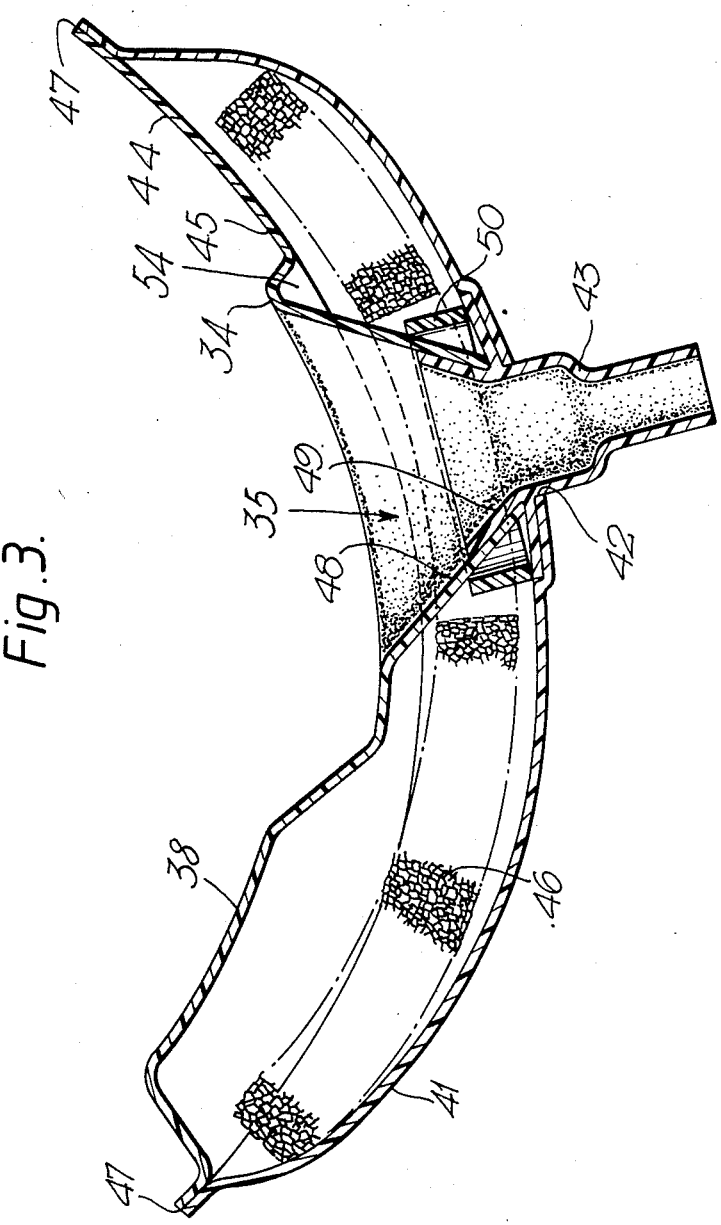

FEMALE EXTERNAL URINAL DEVICE

BACKGROUND OF THE INVENTION

This invention relates to female external urine collection devices.

The problems associated with urinary incontinence with women can be alleviated either by means of a catheter inserted in the urethra or by means of an external device that collects urine after discharge. The use of an internal catheter can present problems of discomfort to the user, difficulties of insertion and an increased risk of infection. In many cases some form of external device is preferred. This can be an absorbent disposable pad worn under the clothes, or some form of device which collects the urine and channels it to a urine receptacle, such as a leg bag. Absorbent pads may not be capable of retaining discharge from a full bladder, can be bulky to wear and are uncomfortable after use when they become damp to the touch. There is also the risk that urine can run off the surface of the pad, before it has time to be absorbed, and can leak around the edge.

BRIEF SUMMARY OF THE INVENTION

It is an object of the present invention to provide a female external urinal device that can be used to alleviate these problems.

According to one aspect of the present invention there is provided a female external urine collection device that is bendable and shaped to extend between the legs of the wearer, the device having an upper surface for contact with the wearer, said upper surface having an upwardly projecting annular wall located to engage around the vulva so that discharge of urine is contained within the wall, an opening through the device within the wall that communicates with an outlet orifice, and the upper surface having a longitudinal ridge member extending posteriorly of the wall and arranged to be located between the buttocks of the user.

The device may include a first tray member and a second member provided with said upper surface, the outlet orifice being provided on the tray member, and the second member having an opening therethrough that aligns with said outlet orifice. The tray member is preferably of a urine-resistant foamed plastics material, the second member being an insert in the tray member and the second member being of an absorbent material. The insert preferably has a urine-resistant layer on the surface of the opening.

The upper surface may be provided on a planar member.

The second member may be a planar member extending across the top of the tray member, the tray member including means for supporting said planar member beneath the planar member. The planar member preferably has a urine-resistant upper surface. The opening in the planar member is preferably sealed with the outlet orifice and the planar member may be sealed around its outer edge with the tray member.

The device may be a single moulding, at least the underside and edge surfaces of the moulding being urine resistant.

Female external urine collection devices in accordance with the present invention will now be described, by way of example, with reference to the accompanying drawings.

BRIEF DESCRIPTION OF THE DRAWINGS

FIG. 3 is a sectional side elevation of an alternative device.

DESCRIPTION OF PREFERRED EMBODIMENTS

Figure 1:
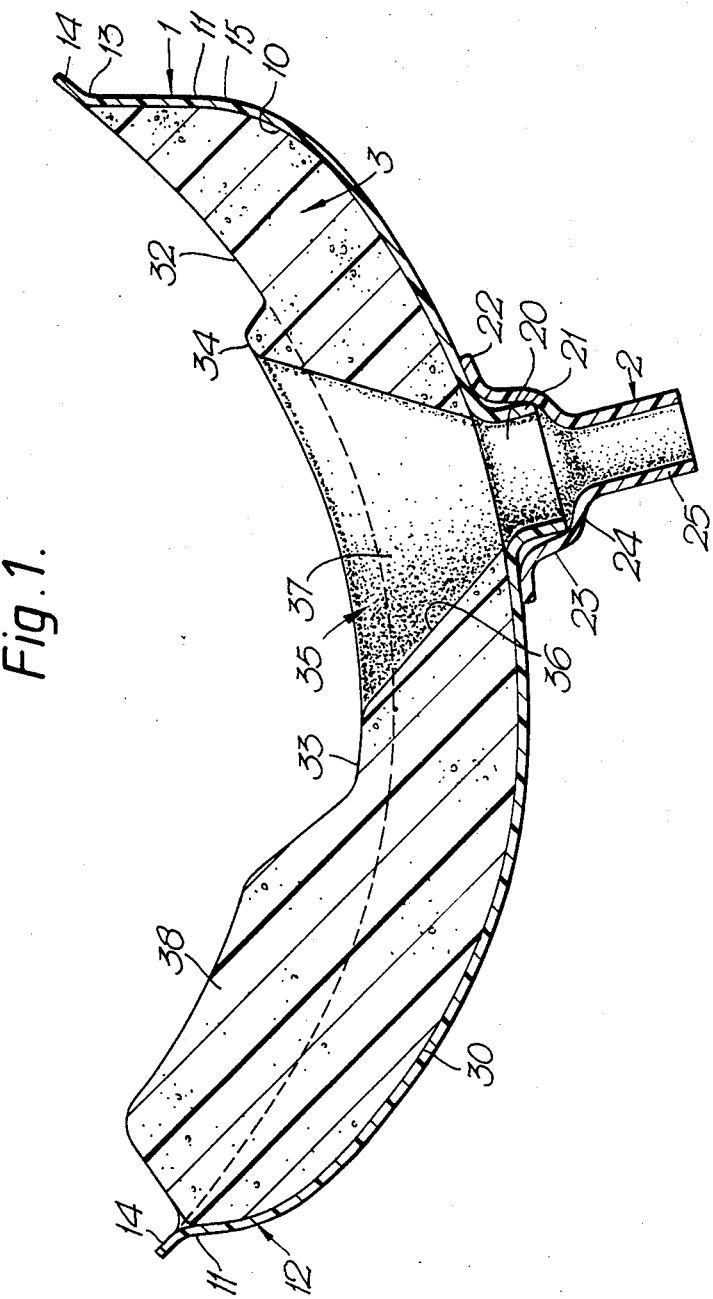
FIG. 1 is a sectional side elevation of one form of device.
Figure 2:
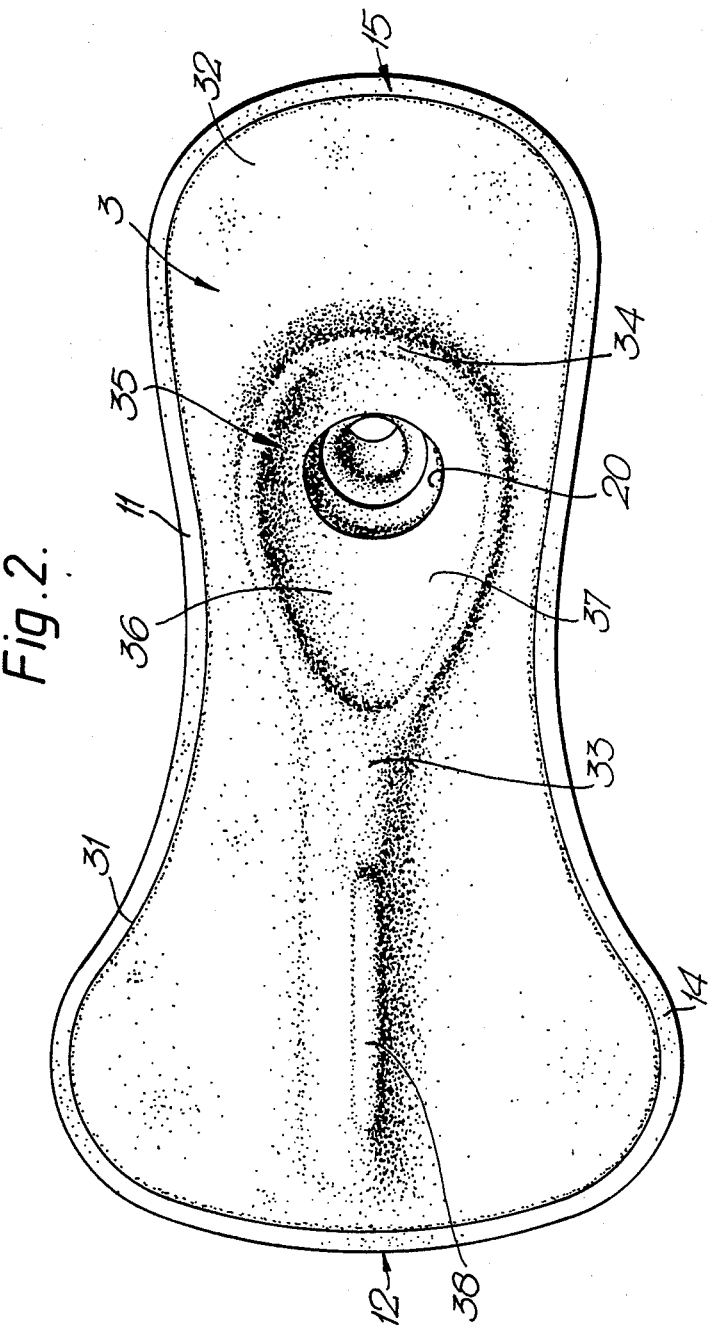
FIG. 2 is a plan view of the device of FIG. 1.

The urine collection device shown in FIGS. 1 and 2 is formed in three parts, namely an outer tray 1, an outlet spout 2 and an absorbent insert 3.

The tray is of a non-absorbent/urine-resistant foamed polyethylene, PVC or EVA and is formed by vacuum moulding from sheet material about 2 mm thick. The tray 1 has a generally oblong shape and is curved upwardly along its longitudinal axis so that its floor 10 is concave longitudinally but flat laterally. Around its edge, the tray 1 has an upwardly projecting wall 11 which gives the tray a depth of about 20 mm along the major part of its length which reduces to about 12 mm at the posterior end 12. The upper edge 13 of the wall 11 is curved outwardly forming a lip 14. In plan view, the posterior end 12 of the tray 1 is rounded with a width of about 104 mm at its widest point. The edge of the tray 1 curves inwardly on both sides to its narrowest width of about 62 mm at a point about 90 mm from its posterior end. The edge of the tray 1 curves outwardly towards its anterior end 15, where it is formed with a rounded end of width about 75 mm. The shape and material of the tray make it soft and semi-rigid but bendable.

An outlet orifice 20 is formed centrally in the floor of the tray 1 at a point about 90 mm from the anterior end 15. The orifice 20 takes the form of a downwardly-projecting nose 21 with a circular section of external diameter of about 20 mm. The outlet spout 2 is sealed to the lower surface of the tray 1 around the nose 21. The spout 2 is a moulding of PVC having a wall thickness of about 2 mm. At its upper end, the spout 2 has a radially extending flange 22, of diameter 42 mm, by which the spout is secured to the tray 1, such as by welding or adhesive. The inner edge of the flange 22 curves downwardly to form a short cylindrical ring section 23 of diameter about 25 mm and length about 7 mm. The lower end of the ring section 23 continues as an inwardly tapering frusto-conical section 24 which communicates with a cylindrical portion 25 of 9 mm internal diameter and length 17 mm. The overall length of the spout is about 33 mm. The material and shape of the spout 2 give the portion 25 a resilience to axial and lateral displacement.

The absorbent insert 3 is a one-piece moulding of a hydrophilic foamed plastics material such as polyurethane (as sold under the trade mark Hypol). The lower surface 30 and the periphery 31 of the insert 3 conform with the floor 10 and wall 11 of the tray 1. The upper surface 32 of the insert 3 lies level with the lip 14 of the tray 1 except for an upwardly projecting surface formation 33. The surface formation 33 takes the form of an annular wall 34 of oval section and of height about 10 mm. The annular wall has, at its upper end, an internal width of 36 mm and length of 60 mm. The wall 34 is located to overlie the orifice 20 in the tray 1 and communicates with it through a generally frusto-conical opening 35 within the wall that extends through the thickness of the insert 3 in alignment with the orifice.

The surface 36 of the frusto-conical opening 35 is treated to render it less absorbent of urine, such as by means of a urine-resistant polyurethane layer formed by a coating 37.

From the posterior end of the wall 34 there extends a longitudinal ridge 38. The ridge 38 projects about 20 mm above the top of the wall of the tray 1. The ridge 38 is of generally triangular section being about 5 mm wide at the top and 20 mm wide at its base.

The insert 3 may be a loose fit in the tray or may be removably secured in the tray such as by means of an adhesive. For example, an adhesive ring on the lower surface of the insert 3 around the opening 35 could be used to form a seal of the opening with the nose 21.

In use, the device is placed between the user's legs with the upper surface 32 of the insert 3 in contact with the periurethral area. The device is positioned such that the wall 34 around the opening 35 contacts around the user's vulva, with the ridge 38 extending in the fold between the buttocks. The ridge 38 serves a dual purpose of helping to locate the device securely against lateral movement and twisting and of helping to prevent any leakage of urine. The device is held in place either by means of elasticated pants (not shown) having an opening through which the spout 2 emerges or by means of straps through slots (not shown) in the edge of the tray. The insert 3 is compressed slightly against the user so that an effective seal is made by the upper edge of the wall 34. The device is sufficiently soft and flexible to enable it to be bent to the shape of the anatomy and to flex during movement of the wearer, without discomfort.

The cylindrical portion 25 of the spout 2 is connected to a urine drainage tube (not shown) which extends to a urine leg bag or other urine receptacle. The resilient nature of the spout 2 enables it to be bent to the side to accommodate the urine tube without the risk of occluding the opening through the spout.

Flow of urine from the urethral opening is channelled through the opening 35 in the insert 3 via the nose 21 and spout 2 into the urine tube and the urine bag.

The urine-resistant coating 37 ensures that most of the urine flows through the opening 35 of the insert 3 without being absorbed. Any leakage of urine into the bottom of the tray 1, under the insert, will be readily absorbed by the lower surface of the insert before it can seep out of the tray. Similarly, any leakage of urine over the top of the wall 34 will be absorbed by the absorbent upper surface 32 of the insert 3.

The urine collection device according to the present invention provides a comfortable device capable of channelling urine with a lower risk of leakage. The insert 3 can be removed from the tray after use and replaced or washed out. This enables the cost of using the device to be kept to a minimum.

Where an absorbent insert is used, it is not essential for the tray to have an opening. For smaller urine discharge, the tray could have a closed floor. In such a construction, the lower end of the opening 35 in the insert would not be sealed with the floor of the tray, so that urine flowing through the opening is free to flow under the insert where it is absorbed by the underside of the insert. The opening through the insert serves to reduce run off from the top of the insert since the urine has a greater time to contact the absorbent surface than with conventional flat absorbent pads.

Various alternative constructions are possible. For example, the device need not have a separate tray and insert, but could be a single moulding with an integral or separate outlet spout. The moulding could be coated on its underside and edge surfaces to be urine resistant, but be absorbent on its upper surface. It is not essential for the urine collection device to be absorbent. The single moulding could be provided with a non-absorbent skin over its entire surface. Preferably the material of the single moulding is hydrophobic.

An alternative, non-absorbent device is shown in FIG. 3. This device has a tray 41, substantially the same as that shown in FIGS. 1 and 2, except that the outlet orifice 42 is formed by a circular aperture in the floor of the tray and has a PVC spout 43 mounted internally of the tray. The device has a moulded planar top 44 formed from the same material as the tray 41 and is typically about 2 mm thick. Alternative urine-resistant materials, or materials with a urine-resistant upper surface 45 could be used. The upper surface 45 of the top has the same profile as the insert 3 shown in FIGS. 1 and 2. Within the tray 41 beneath the top 44 is a support member 46 which takes the form of a pad about 15 mm thick made from a skeletal plastics material such as a skeletal polyester material with a density of 30 kg m sold by Foam Engineers Limited of High Wycombe, England, under reference RB10. The support pad 46 extends beneath the major part of the surface of the top 44 to help space the top 44 from the lower surface of the tray. Increased stiffness can be given to the annular wall 34 and the ridge 38 by filling the recess 54 formed underneath the wall and ridge with a plastics material of the desired stiffness. The top 44 is preferably sealed around its edge 47 to the edge of the tray 41 to prevent urine flowing beneath the top. The materials and construction are such that the device can be bent along its length to conform to the anatomy of the user, with the surface formation on the top 44 being urged firmly into contact with the wearer to give an effective seal.

A urine outlet through the top 44 is provided by a frusto-conical downward projection 48 formed in the top. This projection 48 is sealed with the inside of a frusto-conical extension 49 of the spout 43 so that urine entering the projection 48 flows out through the spout without any leakage into the tray 41. In order to prevent the spout 43 being closed by lateral compression between the legs of the user, a rigid nylon ring 50 embraces the spout inside the tray. In other constructions, the lower end of the projection 48 could be sealed directly to the tray 41 around the orifice 42. These constructions trap air inside the device giving it greater resilience.

In a further alternative device the tray 41 could be dispensed with and the projection 48 of the top could be connected directly to a urine outlet tube. A thin, shaped plate may be required underneath the top 44 to support the annular wall 34 and the ridge 38. The device could be supported by means of straps extending through apertures in the planar top 44 or by elasticated pants.

What we claim is:

1. A female external urine collection device that is bendable and shaped to extend between the legs of the user, wherein the device has an upper surface arranged to contact the user, said upper surface being urine resistant and having an upwardly projecting urine resistant annular wall located to engage around the vulva so that discharge of urine is contained within said wall, an opening through the urine collection device within said wall, an outlet orifice that communicates with said opening, and a urine resistant longitudinal ridge member means extending posteriorly of said wall along said upper surface and arranged to extend in the fold between the buttocks of the user so as thereby to locate the device securely in position.

2. A device according to claim 1, wherein said device comprises a first tray member and a second member provided with said upper surface, wherein the outlet orifice is provided on the tray member, and wherein the said opening extends through the second member in alignment with said outlet orifice.

3. A device according to claim 2, wherein said tray member is of a urine-resistant foamed plastics material.

4. A device according to claim 2, wherein said second member is a planar member, which extends across the top of the tray member, and wherein said tray member includes support means for supporting said planar member beneath the planar member.

5. A device according to claim 4, including means sealing the said opening in the second member with the outlet orifice.

6. A device according to claim 4, wherein said planar member is sealed around its outer edge with the tray member.

7. A device according to claim 1, wherein the said upper surface is provided by a planar member.

* * * * *